(12) United States Patent
Trama et al.

(10) Patent No.: US 7,745,595 B2
(45) Date of Patent: Jun. 29, 2010

(54) **COMPOSITIONS AND METHODS FOR DETECTING *ATOPOBIUM VAGINAE***

(75) Inventors: Jason Trama, Burlington, NJ (US); Martin E. Adelson, Hillsborough, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 241 days.

(21) Appl. No.: 11/502,694

(22) Filed: Aug. 10, 2006

(65) Prior Publication Data

US 2008/0038726 A1     Feb. 14, 2008

(51) Int. Cl.
*C07H 21/04* (2006.01)
*C12Q 1/68* (2006.01)

(52) U.S. Cl. .................. 536/23.1; 536/24.3; 435/6; 435/91.1; 435/91.2

(58) Field of Classification Search .................. None
See application file for complete search history.

(56) References Cited

U.S. PATENT DOCUMENTS 5,474,796 A * 12/1995 Brennan .................. 427/2.13
2001/0053519 A1 * 12/2001 Fodor et al. .................. 435/6
2003/0104410 A1 * 6/2003 Mittmann .................. 435/6
2005/0118625 A1 * 6/2005 Mounts .................. 435/6

FOREIGN PATENT DOCUMENTS

WO     WO0177384     * 10/2001

OTHER PUBLICATIONS

Standford Genome Technology Center *Atopobium vaginae* Genome Project website. (.http://med.stanford.edu/sgtc/research/atopobium_vaginae.html, Jun. 14, 2006).*

* cited by examiner

*Primary Examiner*—Jeanine A Goldberg
(74) *Attorney, Agent, or Firm*—Siu K. Lo

(57) ABSTRACT

Disclosed are oligonucleotides useful in methods for determining whether a sample contains *Atopobium vaginae* or has an increased likelihood of containing *Atopobium vaginae*, an organism which is seen in conjunction with bacterial vaginosis or is a causative agent of bacterial vaginosis. These oligonucleotides, which have nucleotide sequences derived from a segment of the genome of *Atopobium vaginae*, are useful as forward and reverse primers for a polymerase chain reaction using nucleic acids from a biological sample as a template, and as probes for detecting any resultant amplicon. Detection of an amplicon indicates the sample contains *Atopobium vaginae* or has an increased likelihood of containing *Atopobium vaginae*.

6 Claims, No Drawings

COMPOSITIONS AND METHODS FOR DETECTING *ATOPOBIUM VAGINAE*

SUMMARY OF THE INVENTION

*Atopobium vaginae* is an organism which is seen in conjunction with bacterial vaginosis or is a causative agent of bacterial vaginosis. Thus, there is a need for compositions and methods, e.g., oligonucleotides useful as primers and probes in polymerase chain reactions ("PCRs"), for detecting *Atopobium vaginae* in a patient.

OLIGONUCLEOTIDES OF THE INVENTION

An embodiment of the invention is drawn to an isolated oligonucleotide (e.g., a forward primer, a reverse primer, or a probe such as a molecular beacon) capable of hybridizing under highly stringent hybridization conditions to a polynucleotide consisting of the nucleotide sequence of SEQ ID NO:1 or SEQ ID NO:2, wherein the nucleotide sequence of each of SEQ ID NO:1 and SEQ ID NO:2 is comprised by the genome of *Atopobium vaginae*, wherein the nucleotide sequence of SEQ ID NO:2 is the reverse complement of the nucleotide sequence of SEQ ID NO:1.

Highly stringent hybridization conditions include the following conditions: 6×SSC and 65° C.; highly stringent hybridization conditions described in Ausubel et al., 2002, Short Protocols in Molecular Biology, 5$^{th}$ edition, Volumes 1 and 2, John Wiley & Sons, Inc., Hoboken, N.J., the entire contents of which are hereby incorporated by reference; and highly stringent hybridization conditions described in Ausubel et al., 1997, Short Protocols in Molecular Biology, 3$^{rd}$ edition, John Wiley & Sons, Inc., New York, N.Y., the entire contents of which are hereby incorporated by reference. In another embodiment, the oligonucleotide is capable of hybridizing under highly stringent hybridization conditions to a polynucleotide consisting of nucleotides 179 through 196 of SEQ ID NO:2, nucleotides 133 through 170 of SEQ ID NO:2, nucleotides 140 through 163 of SEQ ID NO:2, or nucleotides 179 through 196 of SEQ ID NO:1.

In another embodiment, the oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of a polynucleotide based on the Clustal V or W alignment method using the default parameters, wherein the polynucleotide consists of the nucleotide sequence of SEQ ID NO:1 or SEQ ID NO:2.

Pairwise nucleotide sequence alignments and determination of percent identities are performed using the default parameters of the Clustal V algorithm or the Clustal W algorithm, wherein both algorithms are incorporated into the Power Macintosh MegAlign 6.1 program (DNASTAR, Madison, Wis.). The default parameters for pairwise alignments using the Clustal V algorithm are as follows: Ktuple=1, gap penalty=3, window=5, and diagonals=5. The default parameters for pairwise alignments using the Clustal W algorithm are as follows: gap penalty=10.00 and gap length=0.10. The Clustal V algorithm is described in Higgins et al., 1989, Fast and sensitive multiple sequence alignments on a microcomputer. Computer Applications in the Biosciences 5:151-153, the entire contents of which are hereby incorporated by reference. The Clustal W algorithm is described in Thompson et al., 1994, CLUSTAL W: improving the sensitivity of progressive multiple sequence alignment through sequence weighting, position specific gap penalties and weight matrix choice. Nucleic Acids Research 22:4673-80, the entire contents of which are hereby incorporated by reference. In another embodiment, the oligonucleotide and the segment of the polynucleotide contain the same number of nucleotides.

In another embodiment, the oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to nucleotides 1 through 18 of SEQ ID NO:1, nucleotides 27 through 64 of SEQ ID NO:1, nucleotides 34 through 57 of SEQ ID NO:1, or nucleotides 1 through 18 of SEQ ID NO:2 based on the Clustal V or W alignment method using the default parameters.

In another embodiment, the oligonucleotide consists of a nucleotide sequence comprised by the nucleotide sequence of SEQ ID NO:1 or SEQ ID NO:2. In another embodiment, the oligonucleotide comprises 8, 9, 10, 11, 12, 13, 14, 15, 16, 17, 18, 19, 20, 21, 22, 23, 24, 25, 26, 27, 28, 29, or 30 nucleotides. In another embodiment, the oligonucleotide is from 8 to 50 nucleotides long, from 12 to 24 nucleotides long, from 15 to 50 nucleotides long, or from 25 to 35 nucleotides long. In another embodiment, the oligonucleotide comprises the nucleotide sequence of SEQ ID NO:3, SEQ ID NO:4, or SEQ ID NO:5. In another embodiment, the oligonucleotide consists of the nucleotide sequence of SEQ ID NO:3, SEQ ID NO:4, or SEQ ID NO:5.

OLIGONUCLEOTIDE COMBINATIONS OF THE INVENTION

Another embodiment of the invention is directed to a composition (e.g., a reaction mixture or a kit) containing a first isolated oligonucleotide (e.g., a forward primer) and a second isolated oligonucleotide (e.g., a reverse primer). In another embodiment, the first oligonucleotide is capable of hybridizing under highly stringent hybridization conditions to a polynucleotide consisting of the nucleotide sequence of SEQ ID NO:2. In another embodiment, the second oligonucleotide is capable of hybridizing under highly stringent hybridization conditions to a polynucleotide consisting of the nucleotide sequence of SEQ ID NO:1. In another embodiment, the first oligonucleotide is capable of hybridizing under highly stringent hybridization conditions to a polynucleotide consisting of nucleotides 179 through 196 of SEQ ID NO:2. In another embodiment, the second oligonucleotide is capable of hybridizing under highly stringent hybridization conditions to a polynucleotide consisting of nucleotides 179 through 196 of SEQ ID NO:1.

In another embodiment, the first oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of a first polynucleotide based on the Clustal V or W alignment method using the default parameters, wherein the first polynucleotide consists of the nucleotide sequence of SEQ ID NO:1. In another embodiment, the first oligonucleotide and the segment of the first polynucleotide contain the same number of nucleotides. In another embodiment, the second oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of a second polynucleotide based on the Clustal V or W alignment method using the default parameters, wherein the second polynucleotide consists of the nucleotide sequence of SEQ ID NO:2. In another embodiment, the second oligonucleotide and the segment of the second polynucleotide contain the same number of nucleotides.

In another embodiment, the first oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to nucleotides 1 through 18 of SEQ ID NO:1 based on the Clustal V or W alignment method using the default parameters. In another embodiment, the second oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to nucleotides 1 through 18 of SEQ ID NO:2 based on the Clustal V or W alignment method using the default parameters.

In another embodiment, the first oligonucleotide consists of a nucleotide sequence comprised by the nucleotide sequence of SEQ ID NO:1. In another embodiment the second oligonucleotide consists of a nucleotide sequence comprised by the nucleotide sequence of SEQ ID NO:2. In another embodiment, the first or second oligonucleotide comprises 8, 9, 10, 11, 12, 13, 14, 15, 16, 17, 18, 19, 20, 21, 22, 23, 24, 25, 26, 27, 28, 29, or 30 nucleotides. In another embodiment, the first or second oligonucleotide is from 8 to 50 nucleotides long or from 12 to 24 nucleotides long. In another embodiment, the first oligonucleotide comprises the nucleotide sequence of SEQ ID NO:3. In another embodiment, the first oligonucleotide consists of the nucleotide sequence of SEQ ID NO:3. In another embodiment, the second oligonucleotide comprises the nucleotide sequence of SEQ ID NO:4. In another embodiment, the second oligonucleotide consists of the nucleotide sequence of SEQ ID NO:4.

METHODS OF THE INVENTION

Another embodiment of the invention concerns a method for determining whether a sample (e.g., a biological sample such as cervicovaginal-swab specimen) contains *Atopobium vaginae* or has an increased likelihood of containing *Atopobium vaginae*, wherein the method comprises the following: (a) providing a vessel containing a composition, wherein the composition contains first and second primers and a nucleic acid from the sample, wherein the composition is capable of amplifying by a polymerase chain reaction a segment of the nucleic acid to produce an amplicon, wherein production of the amplicon is primed by the first and second primers, wherein the first primer is capable of hybridizing under highly stringent hybridization conditions to a polynucleotide consisting of the nucleotide sequence of SEQ ID NO:2, wherein the second primer is capable of hybridizing under highly stringent hybridization conditions to a polynucleotide consisting of the nucleotide sequence of SEQ ID NO:1; (b) incubating the vessel under conditions allowing production of the amplicon if the sample contains *Atopobium vaginae*, and (c) determining that the sample contains *Atopobium vaginae* if the amplicon is detected or that the sample has an increased likelihood of containing *Atopobium vaginae* if the amplicon is detected, or determining that the sample does not contain *Atopobium vaginae* if the amplicon is not detected or that the sample does not have an increased likelihood of containing *Atopobium vaginae* if the amplicon is not detected.

In another embodiment, the first primer is capable of hybridizing under highly stringent hybridization conditions to a polynucleotide consisting of nucleotides 179 through 196 of SEQ ID NO:2. In another embodiment, the second primer is capable of hybridizing under highly stringent hybridization conditions to a polynucleotide consisting of nucleotides 179 through 196 of SEQ ID NO:1.

In another embodiment, the first primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of a first polynucleotide based on the Clustal V or W alignment method using the default parameters, wherein the first polynucleotide consists of the nucleotide sequence of SEQ ID NO:1. In another embodiment, the first primer and the segment of the first polynucleotide contain the same number of nucleotides. In another embodiment, the second primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of a second polynucleotide based on the Clustal V or W alignment method using the default parameters, wherein the second polynucleotide consists of the nucleotide sequence of SEQ ID NO:2. In another embodiment, the second primer and the segment of the second polynucleotide contain the same number of nucleotides.

In another embodiment, the first primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to nucleotides 1 through 18 of SEQ ID NO:1 based on the Clustal V or W alignment method using the default parameters. In another embodiment, the second primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to nucleotides 1 through 18 of SEQ ID NO:2 based on the Clustal V or W alignment method using the default parameters.

In another embodiment, the first primer consists of a nucleotide sequence comprised by the nucleotide sequence of SEQ ID NO:1. In another embodiment the second primer consists of a nucleotide sequence comprised by the nucleotide sequence of SEQ ID NO:2. In another embodiment, the first or second primer comprises 8, 9, 10, 11, 12, 13, 14, 15, 16, 17, 18, 19, 20, 21, 22, 23, 24, 25, 26, 27, 28, 29, or 30 nucleotides. In another embodiment, the first or second primer is from 8 to 50 nucleotides long or from 12 to 24 nucleotides long. In another embodiment, the first primer comprises the nucleotide sequence of SEQ ID NO:3. In another embodiment, the first primer consists of the nucleotide sequence of SEQ ID NO:3. In another embodiment, the second primer comprises the nucleotide sequence of SEQ ID NO:4. In another embodiment, the second primer consists of the nucleotide sequence of SEQ ID NO:4. In another embodiment, the amplicon comprises 16, 32, 64, 128, or 196 nucleotide base pairs. In another embodiment, the amplicon consists of 196 nucleotides base pairs. In another embodiment, the amplicon contains a single EcoRI recognition site. In another embodiment, one strand of the amplicon consists of the nucleotide sequence of SEQ ID NO:1, and the other strand of the amplicon consists of the nucleotide sequence of SEQ ID NO:2.

Optionally, in (b) of the method, the vessel contains an oligonucleotide probe (e.g., a molecular beacon) capable of detecting the amplicon if the amplicon is produced in (b). In another embodiment, the oligonucleotide probe is capable of hybridizing under highly stringent hybridization conditions to a polynucleotide consisting of the nucleotide sequence of SEQ ID NO:1 or SEQ ID NO:2.

In another embodiment, the oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to a segment of a polynucleotide based on the Clustal V or W alignment method using the default parameters, wherein the polynucleotide consists of the nucleotide sequence of SEQ ID NO:1 or SEQ ID NO:2. In another embodiment, the oligonucleotide probe and the segment of the polynucleotide contain the same number of nucleotides.

In another embodiment, the oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to nucleotides 27 through 64 or nucleotides 34 through 57 of SEQ ID NO:1 based on the Clustal V or W alignment method using the default parameters.

In another embodiment, the oligonucleotide probe comprises 8, 9, 10, 11, 12, 13, 14, 15, 16, 17, 18, 19, 20, 21, 22, 23, 24, 25, 26, 27, 28, 29, or 30 nucleotides. In another embodiment, the oligonucleotide probe is from 15 to 50 nucleotides long or from 25 to 35 nucleotides long. In another embodiment, the oligonucleotide probe comprises the nucleotide sequence of SEQ ID NO:5, SEQ ID NO:6, or SEQ ID NO:7. In another embodiment, the oligonucleotide probe consists of the nucleotide sequence of SEQ ID NO:5. In another embodiment, a 6-carboxy-fluorescein moiety is attached to the 5' end of the oligonucleotide probe, a Black Hole Quencher 1 moiety is attached to the 3' end of the oligonucleotide probe, and the amplicon is detected by the oligonucleotide probe during real-time PCR. In another embodiment, the amplicon is detected by gel electrophoresis after the PCR is completed. In another embodiment, the amplicon is cleaved with EcoRI after the PCR is completed, and the resulting cleavage products are subjected to gel electrophoresis.

DETAILED DESCRIPTION

The following examples illustrate the use of the methods and compositions of the invention. These examples are set forth by way of illustration only, and nothing therein shall be taken as a limitation upon the overall scope of the invention.

EXAMPLE 1

Conditions for the PCR

Except for positive and negative controls, and a PCR used to generate a positive-control standard DNA (see Example 2), each PCR was attempted in a volume of 25 µL containing the following: DNA extracted from a sample (e.g., 25 ng), 300 nM of a first primer consisting of the nucleotide sequence of SEQ ID NO:3 ("primer AVB2 F"); 300 nM of a second primer consisting of the nucleotide sequence of SEQ ID NO:4 ("primer AVB2 R"); 200 nM of an oligonucleotide probe consisting of the nucleotide sequence of SEQ ID NO:5, wherein a 6-carboxy-fluorescein moiety and a Black Hole Quencher 1 moiety were attached to the 5' end and 3' end, respectively, of the oligonucleotide probe ("probe AVBeaconPr"); and 1×iTaq custom supermix (Bio-Rad Laboratories, Inc., Hercules, Calif.), wherein the 2× stock solution of the iTaq custom supermix contained 120 U/ml of iTaq DNA polymerase, 80 mM Tris-HCl (pH 8.4), 200 mM KCl, 6 mM $MgCl_2$, 400 µM dATP, 400 µM dCTP, 400 µM dGTP, 800 µM dUTP, 80 U/ml of UNG, and proprietary Bio-Rad Laboratories stabilizers. Probe AVBeaconPr was present in the reaction mixture to monitor real-time synthesis of the amplicon resulting from each successful PCR. The primer AVB2 F, the primer AVB2 R, and the probe AVBeaconPr were synthesized by Integrated DNA Technologies (Stokie, Ill.).

Nucleotide sequences of additional first primers, second primers, and oligonucleotide probes are determined from the nucleotide sequences of SEQ ID NO:1 and SEQ ID NO:2 using computer programs such as Assay Design Software 1.0.6 (Biotage, Uppsala, Sweden) and Beacon Designer 4.02 (Build 402003) (PREMIER Biosoft International, Palo Alto, Calif.).

PCRs were conducted using the Rotor-Gene 3000 platform (Corbett Research, Sydney, Australia). Parameters for each PCR were as follows: an initial incubation at 50° C. for 2 minutes to activate UNG, followed by an incubation at 95° C. for 2 minutes to initially denature the DNA, inactivate the UNG, and activate the iTaq DNA polymerase. Next, 35 cycles of denaturation (95° C. for 20 seconds), a first annealing and extension (55° C. for 20 seconds), and a second annealing and extension (72° C. for 30 seconds) were performed with fluorescence acquisition (excitation at 470 nM and emission at 510 nM) immediately following the first annealing and extension step. Fluorescence curves were analyzed with dynamic-tube normalization, slope correction, and automatic threshold determination by a best-fit line of three concentrations (in most cases) of the positive-control standard DNA using Rotor-Gene version 5.0 software (Corbett Research, Sydney, Australia). The three concentrations of the positive-control standard DNA were either three dilutions of genomic DNA extracted from an isolate of *Atopobium vaginae* purchased from the American Type Culture Collection (catalog number BAA-55; ATCC®; Manassas, Va.), or $1 \times 10^3$, $1 \times 10^5$, and $1 \times 10^7$ copies per reaction of pAvagJZ (a plasmid which is described in Example 2). In one case (see Table 1), the positive-control standard DNA was 25 ng per reaction mixture of genomic DNA extracted from *Atopobium vaginae* ATCC® No. BAA-55.

EXAMPLE 2

Positive-Control Standard DNA for the PCR

A positive-control standard DNA was obtained by the PCR amplification of 200 ng of DNA extracted from *Atopobium*

*vaginae* ATCC® No. BAA-55. Parameters for this PCR were as follows: an initial incubation at 94° C. for 2 minutes; followed by 35 cycles of incubation at 95° C. for 15 seconds, 54° C. for 10 seconds, and 60° C. for 1 minute; followed by a final incubation at 72° C. for 10 minutes. All other conditions for this reaction were as described in Example 1. The resulting amplicon was cloned into the pCR®2.1-TOPO® vector (Invitrogen, Carlsbad, Calif.) to produce pAvagJZ, which was used as the positive-control standard DNA. The nucleotide sequence of the first strand and the nucleotide sequence of the second strand of this amplicon are shown in SEQ ID NO:1 and SEQ ID NO:2, respectively.

EXAMPLE 3

Specificity of the PCR

The specificity of the PCR utilizing the combination of primer AVB2 F, primer AVB2 R, and probe AVBeaconPr was assessed by attempting to conduct real-time PCRs in reaction mixtures containing DNA from a number of microorganisms purchased from ATCC® that were not *Atopobium vaginae*; however, several of these isolates were species of the *Atopobium* genus. No PCR amplification was observed in any of these reaction mixtures (see Table 1).

TABLE 1

| Sample | Results |
| --- | --- |
| *Atopobium minutum* (ATCC ® No. 33267) | −* |
| *Atopobium rimae* (ATCC ® No. 49626) | − |
| *Atopobium parvulum* (ATCC ® No. 33793) | − |
| *Atopobium fossor* (ATCC ® No. 43386) | − |
| *Actinomyces israelii* (ATCC ® No. 10049) | − |
| *Actinomyces bovis* (ATCC ® No. 13683) | − |
| *Coriobacterium glomerans* (ATCC ® No. 49209) | − |
| Positive Control (25 ng of genomic DNA from *Atopobium vaginae*) | +** |
| Negative Control (no template DNA) | − |

*A "−" indicates the absence of PCR amplification in the sample.
**A "+" indicates the presence of PCR amplification in the sample.

Additionally, the specificity of the PCR utilizing the combination of primer AVB2 F, primer AVB2 R, and probe AVBeaconPr was assessed by attempting to conduct real-time PCRs in cocktail format, wherein each of two reaction mixtures contained DNA extracted from four or five types of pathogen as summarized in Table 2; each pathogen was purchased from ATCC®, except for *Haemophilis parainfluenza*, *Candida lusitaneae*, and *Legionella pneumophila*, which were purchased from MicroBioLogics Inc. (Saint Cloud, Minn.).

TABLE 2

| | Number |
| --- | --- |
| Cocktail 1 | |
| *Gardnerella vaginalis* | ATCC ® No. 14018 |
| *Neisseria gonorrhoeae* | ATCC ® No. 27628 |
| *Trichomonas vaginalis* | ATCC ® No. 30246 |
| *Ureaplasma urealyticum* | ATCC ® No. 27618 |
| Cocktail 2 | |
| *Bacteroides fragilis* | ATCC ® No. 23745 |
| *Mobiluncus curtisii* | ATCC ® No. 35241 |
| *Mobiluncus mulieris* | ATCC ® No. 35243 |
| HTLV-I | ATCC ® No. CRL-8294 |
| Human herpesvirus 6B | ATCC ® No. VR-1467 |

TABLE 2-continued

| | Number |
| --- | --- |
| Cocktail 3 | |
| Herpes simplex virus 1 | ATCC ® No. VR-539 |
| Herpes simplex virus 2 | ATCC ® No. VR-734 |
| Human Papillomavirus | ATCC ® No. CRL-1550 |
| Epstein-Barr virus | ATCC ® No. CCL-86 |
| Cytomegalovirus | ATCC ® No. VR-807 |
| Cocktail 4 | |
| *Candida albicans* | ATCC ® No. 11651 |
| *Candida glabrata* | ATCC ® No. 2001 |
| *Candida parapsilosis* | ATCC ® No. 22019 |
| *Candida tropicalis* | ATCC ® No. 13803 |
| *Aspergillus fumigatus* | ATCC ® No. 14110 |
| Cocktail 5 | |
| *Mycoplasma fermentans* | ATCC ® No. 15474 |
| *Mycoplasma pneumoniae* | ATCC ® No. 15377 |
| *Mycoplasma genitalium* | ATCC ® No. 33530 |
| *Mycoplasma penetrans* | ATCC ® No. 55252 |
| *Mycoplasma hominis* | ATCC ® No. 14027 |
| Cocktail 6 | |
| Human herpesvirus-8 | ATCC ® No. CRL-2230 |
| Adenovirus | ATCC ® No. VR-1 |
| Coxsackievirus | ATCC ® No. VR-184 |
| *Crytococcus neoformans* | ATCC ® No. 2344 |
| *Babesia microti* | ATCC ® No. 30222 |
| Cocktail 7 | |
| *Chlamydia pneumoniae* | ATCC ® No. VR-1356 |
| *Helicobacter pylori* | ATCC ® No. 43579 |
| *Brucella ovis* | ATCC ® No. 25840 |
| *Borrelia burgdorferi* | ATCC ® No. 35210 |
| Canine herpesvirus | ATCC ® No. VR-552 |
| Cocktail 8 | |
| *Bartonella henselae* | ATCC ® No. 49882 |
| *Bartonella bacilliformis* | ATCC ® No. 35656 |
| *Bartonella quintana* | ATCC ® No. 51694 |
| *Trichosporan cutaneum* | ATCC ® No. 4151 |
| Cocktail 9 | |
| Influenza virus A | ATCC ® No. VR-1520 |
| *Haemophilus parainfluenza* | MicroBioLogics No. 0411 |
| Human rhinovirus 6 | ATCC ® No. VR-1116 |
| Human rhinovirus 11 | ATCC ® No. VR-1121 |
| Adenovirus type 10 | ATCC ® No. VR-11 |
| Cocktail 10 | |
| *Candida krusei* | ATCC ® No. 14243 |
| *Candida lusitaniae* | MicroBioLogics No. 0774P |
| *Candida dubliniensis* | ATCC ® No. MYA-179 |
| *Candida utilis* | ATCC ® No. 9226 |
| Cocktail 11 | |
| *Legionella pneumophila* | MicroBioLogics No. 0211 |
| Influenza B virus | ATCC ® No. VR-101 |
| Parainfluenza 2 | ATCC ® No. VR-1381 |
| Parainfluenza 3 | ATCC ® No. VR-93 |

No PCR amplification was observed in either of the two reaction mixtures containing DNA from Cocktail 1, 2, 3, 5, 6, 7, 8, 9, 10, or 11. However, a miniscule amount of PCR amplification appeared to have taken place in each of the two reaction mixtures containing DNA from Cocktail 4; specifically, according to calculations, one amplicon copy was detected in each of these two reaction mixtures after the PCR was attempted (see Table 3).

TABLE 3

| Sample | Results |
| --- | --- |
| Cocktail 1 - Sample 1 | −* |
| Cocktail 1 - Sample 2 | − |
| Cocktail 2 - Sample 1 | − |
| Cocktail 2 - Sample 2 | − |
| Cocktail 3 - Sample 1 | − |
| Cocktail 3 - Sample 2 | − |
| Cocktail 4 - Sample 1 | +** (one amplicon copy) |
| Cocktail 4 - Sample 2 | + (one amplicon copy) |
| Cocktail 5 - Sample 1 | − |
| Cocktail 5 - Sample 2 | − |
| Cocktail 6 - Sample 1 | − |
| Cocktail 6 - Sample 2 | − |
| Cocktail 7 - Sample 1 | − |
| Cocktail 7 - Sample 2 | − |
| Cocktail 8 - Sample 1 | − |
| Cocktail 8 - Sample 2 | − |
| Cocktail 9 - Sample 1 | − |
| Cocktail 9 - Sample 2 | − |
| Cocktail 10 - Sample 1 | − |
| Cocktail 10 - Sample 2 | − |
| Cocktail 11 - Sample 1 | − |
| Cocktail 11 - Sample 2 | − |
| Positive Control (1:10 dilution of genomic DNA from *Atopobium vaginae*) | + |
| Positive Control (1:100 dilution of genomic DNA from *Atopobium vaginae*) | + |
| Positive Control (1:1000 dilution of genomic DNA from *Atopobium vaginae*) | + |
| Negative Control (no template DNA) | − |

*A "−" indicates the absence of PCR amplification in the sample.
**A "+" indicates the presence of PCR amplification in the sample.

To determine which pathogen was responsible for the possible PCR amplification of DNA from Cocktail 4, PCRs were attempted using DNA from each of two isolates of *Candida albicans*, *Candida glabrata*, *Candida parapsilosis*, *Candida tropicalis*, and *Aspergillus fumigatus* in an individual reaction mixture rather than using DNA from all five of these pathogens in one reaction mixture. No PCR amplification was observed in the reaction mixture containing DNA from *Candida glabrata*, *Candida parapsilosis*, *Candida tropicalis*, or *Aspergillus fumigatus*. However, a miniscule amount of PCR amplification appeared to have taken place in each of two reaction mixtures containing DNA from *Candida albicans* ATCC® No. 11651; specifically, according to calculations, five amplicon copies were detected in each of these two reaction mixtures after the PCR was attempted, yet no PCR amplification was observed in the reaction mixture containing DNA from *Candida albicans* ATCC® No. 90028 (see Table 4).

TABLE 4

| Sample | Results |
| --- | --- |
| *Candida albicans* (ATCC ® No. 11651) - Sample 1 | +* (five amplicon copies) |
| *Candida albicans* (ATCC ® No. 11651) - Sample 2 | + (five amplicon copies) |
| *Candida albicans* (ATCC ® No. 90028) | −** |
| *Candida glabrata* (ATCC ® No. 2001) | − |
| *Candida parapsilosis* (ATCC ® No. 22019) | − |
| *Candida tropicalis* (ATCC ® No. 13803) | − |
| *Aspergillus fumigatus* (ATCC ® No. 14110) | − |
| Positive Control (1:10 dilution of genomic DNA from *Atopobium vaginae*) | + |
| Positive Control (1:100 dilution of genomic DNA from *Atopobium vaginae*) | + |
| Positive Control (1:1000 dilution of genomic DNA from *Atopobium vaginae*) | + |
| Negative Control (no template DNA) | − |

*A "+" indicates the presence of PCR amplification in the sample.
**A "−" indicates the absence of PCR amplification in the sample.

Nevertheless, as summarized in Table 5, no PCR amplification was observed in five additional reaction mixtures containing DNA from *Candida albicans* isolated from five respective cervicovaginal-swab specimens by passage of each isolate on selective ChromAgar *Candida* plates (Becton Dickinson Microbiology Systems, Cockeysville, Md.).

TABLE 5

| Sample | Results |
| --- | --- |
| *Candida albicans* - Clinical Sample 1 | −* |
| *Candida albicans* - Clinical Sample 2 | − |
| *Candida albicans* - Clinical Sample 3 | − |
| *Candida albicans* - Clinical Sample 4 | − |
| *Candida albicans* - Clinical Sample 5 | − |
| Positive Control ($1 \times 10^3$ copies of pAvagJZ) | +** |
| Positive Control ($1 \times 10^5$ copies of pAvagJZ) | + |
| Positive Control ($1 \times 10^7$ copies of pAvagJZ) | + |
| Negative Control (no template DNA) | − |

*A "−" indicates the absence of PCR amplification in the sample.
**A "+" indicates the presence of PCR amplification in the sample.

The PCR amplification of DNA from Samples 1 and 2 of Cocktail 4 reported in Table 3 and from Samples 1 and 2 of *Candida albicans* reported in Table 4 was attributed to contamination of *Candida albicans* ATCC® No. 11651 with *Atopobium vaginae*. In fact, according to ATCC®, *Candida albicans* ATCC® No. 11651 was obtained from lung pus. On the other hand, *Candida albicans* ATCC® No. 90028 was obtained from blood.

EXAMPLE 4

Precision of the PCR

Each of five technicians independently assessed the precision of the PCR utilizing the combination of primer AVB2 F, primer AVB2 R, and probe AVBeaconPr by attempting to conduct real-time PCRs using DNA obtained from cervicovaginal-swab specimens. Specifically, each technician tested six reaction mixtures containing DNA purified from a cervical-swab specimen known to contain *Atopobium vaginae* and six reaction mixtures containing DNA purified from a cervical-swab specimen known to be free of *Atopobium vaginae*. As summarized in Table 6, all five technicians correctly determined which of the twelve reaction mixtures contained DNA from *Atopobium vaginae* and which did not, even though they did not know the identity of the template DNA in each reaction mixture before attempting to conduct the PCRs.

TABLE 6

| | | Technician | | | | |
| --- | --- | --- | --- | --- | --- | --- |
| Sample | Expected | A | B | C | D | E |
| 1 | +* | + | + | + | + | + |
| 2 | + | + | + | + | + | + |

TABLE 6-continued

| Sample | Expected | Technician | | | | |
|---|---|---|---|---|---|---|
| | | A | B | C | D | E |
| 3 | −** | − | − | − | − | − |
| 4 | − | − | − | − | − | − |
| 5 | − | − | − | − | − | − |
| 6 | + | + | + | + | + | + |
| 7 | + | + | + | + | + | + |
| 8 | − | − | − | − | − | − |
| 9 | + | + | + | + | + | + |
| 10 | + | + | + | + | + | + |
| 11 | − | − | − | − | − | − |
| 12 | − | − | − | − | − | − |

TABLE 6-continued

| Sample | Expected | Technician | | | | |
|---|---|---|---|---|---|---|
| | | A | B | C | D | E |
| Positive Control (1 × $10^3$ copies of pAvagJZ) | + | + | + | + | + | + |
| Positive Control (1 × $10^5$ copies of pAvagJZ) | + | + | + | + | + | + |
| Positive Control (1 × $10^7$ copies of pAvagJZ) | + | + | + | + | + | + |
| Negative Control (no template DNA) | − | − | − | − | − | − |

*A "+" indicates the presence of DNA of *Atopobium vaginae* in the sample.
**A "−" indicates the absence of DNA of *Atopobium vaginae* in the sample.

The invention claimed is:

1. An isolated oligonucleotide sequence selected from the group consisting of SEQ ID NO: 3, SEQ ID NO: 4 and SEQ ID NO: 5.

2. An isolated oligonucleotide sequence selected from the group consisting of SEQ ID: 1 and SEQ ID NO: 2.

3. A composition comprising a first and a second isolated oligonucleotide, wherein the first oligonucleotide comprises SEQ ID NO: 3 and wherein the second oligonucleotide comprises SEQ ID NO: 4.

4. A method for determining whether a sample contains *Atopobium vaginae* or has an increased likelihood of containing *Atopobium vaginae* comprising:
   (a) providing a vessel containing a composition,
      wherein the composition containing first and second primers, and a nucleic acid from the sample,
      wherein the composition is capable of amplifying, by a polymerase chain reaction, a segment of the nucleic acid to produce an amplicon,
      wherein production of the amplicon is primed by the first and second primers,
      wherein the first primer is SEQ ID NO: 3, and
      wherein the second primer is SEQ ID NO: 4,
   (b) incubating the vessel under conditions allowing production of the amplicon if the sample contains *Atopobiuim vaginae*, and
   (c) determining that the sample contains *Atopobium vaginae* if the amplicon is detected or that the sample has an increased likelihood of containing *Atopobium vaginae* is the amplicon is detected, or determining that the sample does not contain *Atopobium vaginae* if the amplicon is not detected or that the sample does not have an increased likelihood of containing *Atopobium vaginae* if the amplicon is not detected.

5. The method of claim 4, wherein, in (b), the vessel contains an oligonucleotide probe capable of detecting the amplicon if the amplicon is produced in (b).

6. A composition comprising a first, a second and a third isolated oligonucleotide, wherein the first oligonucleotide comprises SEQ ID NO: 3, the second oligonucleotide comprises SEQ ID NO: 4, and the third oligonucleotide comprises SEQ ID NO: 5.

* * * * *

SEQUENCE LISTING

<160> NUMBER OF SEQ ID NOS: 7

<210> SEQ ID NO 1
<211> LENGTH: 196
<212> TYPE: DNA
<213> ORGANISM: Atopobium vaginae

<400> SEQUENCE: 1
cagcgttcct gttactccaa aatgaggaat agaattccac ggttgcacat aacatgcaag      60
cataagacct gcgcataaaa atgcaagacc attcacgaca aaatttccgt aacgattcat     120
aagcttaatt ggctgaatag ccaaaatcgc agcagcagtt gcgcacgcca taccccacgc     180
aagaccttca agtggc                                                    196

<210> SEQ ID NO 2
<211> LENGTH: 196
<212> TYPE: DNA
<213> ORGANISM: Atopobium vaginae

<400> SEQUENCE: 2
gccacttgaa ggtcttgcgt ggggtatggc gtgcgcaact gctgctgcga ttttggctat      60
tcagccaatt aagcttatga atcgttacgg aaattttgtc gtgaatggtc ttgcattttt     120
atgcgcaggt cttatgcttg catgttatgt gcaaccgtgg aattctattc ctcattttgg     180
agtaacagga acgctg                                                    196

<210> SEQ ID NO 3
<211> LENGTH: 18
<212> TYPE: DNA
<213> ORGANISM: Atopobium vaginae

<400> SEQUENCE: 3
cagcgttcct gttactcc                                                   18

<210> SEQ ID NO 4
<211> LENGTH: 18
<212> TYPE: DNA
<213> ORGANISM: Atopobium vaginae

<400> SEQUENCE: 4
gccacttgaa ggtcttgc                                                   18

```
<210> SEQ ID NO 5
<211> LENGTH: 38
<212> TYPE: DNA
<213> ORGANISM: Atopobium vaginae

<400> SEQUENCE: 5
cgcgatcatt ccacggttgc acataacatg cgatcgcg                               38

<210> SEQ ID NO 6
<211> LENGTH: 4
<212> TYPE: DNA
<213> ORGANISM: Atopobium vaginae

<400> SEQUENCE: 6 attc                                                                     4

<210> SEQ ID NO 7
<211> LENGTH: 6
<212> TYPE: DNA
<213> ORGANISM: Atopobium vaginae

<400> SEQUENCE: 7 gaattc                                                                   6
```